(12) United States Patent
Farr (10) Patent No.: US 8,308,769 B2
(45) Date of Patent: Nov. 13, 2012

(54) IMPLANT DEVICE AND METHOD FOR INTERSPINOUS DISTRACTION

(75) Inventor: Morteza M. Farr, Santa Cruz, CA (US)

(73) Assignee: Innovative Spine LLC., Clovis, CA (US)

( * ) Notice: Subject to any disclaimer, the term of this patent is extended or adjusted under 35 U.S.C. 154(b) by 288 days.

(21) Appl. No.: 12/437,513

(22) Filed: May 7, 2009

(65) Prior Publication Data

US 2009/0281626 A1  Nov. 12, 2009

Related U.S. Application Data

(60) Provisional application No. 61/126,863, filed on May 7, 2008.

(51) Int. Cl.
*A61B 17/70* (2006.01)
(52) U.S. Cl. ............................ 606/249; 606/90; 606/105
(58) Field of Classification Search .......... 606/246–279, 606/90, 105; 623/17.11–17.16
See application file for complete search history.

(56) References Cited

U.S. PATENT DOCUMENTS

| | | | | |
|---|---|---|---|---|
| 6,395,034 | B1* | 5/2002 | Suddaby | 623/17.15 |
| 7,229,420 | B2* | 6/2007 | Sakal et al. | 600/573 |
| 2003/0040746 | A1* | 2/2003 | Mitchell et al. | 606/61 |
| 2005/0245937 | A1* | 11/2005 | Winslow | 606/90 |
| 2006/0247640 | A1* | 11/2006 | Blackwell et al. | 606/71 |
| 2007/0043374 | A1* | 2/2007 | Evans | 606/86 |
| 2007/0276500 | A1* | 11/2007 | Zucherman et al. | 623/17.16 |
| 2007/0282443 | A1* | 12/2007 | Globerman et al. | 623/17.11 |
| 2008/0021462 | A1* | 1/2008 | Trieu | 606/61 |
| 2008/0114455 | A1* | 5/2008 | Lange et al. | 623/17.16 |
| 2008/0183218 | A1* | 7/2008 | Mueller et al. | 606/280 |
| 2008/0300686 | A1* | 12/2008 | Khoo | 623/17.11 |
| 2009/0306777 | A1* | 12/2009 | Widmer et al. | 623/13.14 |
| 2010/0241166 | A1* | 9/2010 | Dwyer et al. | 606/249 |

* cited by examiner

*Primary Examiner* — Eduardo C Robert
*Assistant Examiner* — Christina Negrelli
(74) *Attorney, Agent, or Firm* — GSS Law Group (57) ABSTRACT

Improved implant devices and methods for interspinous distraction distribute the load of interspinous distraction so that the entire load is not bearing on the interspinous surfaces. The implant device has a narrow midsection and two wider, flange-shaped outer sections. The wider, flange-shaped outer sections can be tightened to bear against the thicker bony portions of the spinous processes to support some of the load. Optionally, the wider, flange-shaped outer sections can be configured with pins that will penetrate and engage the thicker bony portions of the spinous processes, which will increase the load bearing potential of the wider, flange-shaped outer sections. Additionally, the wider, flange-shaped outer sections and the pins will help to stabilize the joint. The joint stabilization may help to prevent further dislocation of the vertebra that occurs with spondylolisthesis.

15 Claims, 7 Drawing Sheets

IMPLANT DEVICE AND METHOD FOR INTERSPINOUS DISTRACTION

CROSS REFERENCE TO OTHER APPLICATIONS

This application claims benefit of U.S. Provisional application No. 61/126,863, filed on May 7, 2008. This and all patents and patent application referred to herein are hereby incorporated by reference.

FIELD OF THE INVENTION

The present invention relates generally to implantable medical devices. More particularly, it relates to an implantable medical device and method of interspinous distraction for treatment of spinal stenosis.

BACKGROUND OF THE INVENTION

Spinal stenosis is narrowing of the spinal canal, lateral recess or neural foramen resulting in neural compression. The clinical symptoms of spinal stenosis include extremity pain, radiculopathy, sensory or motor deficit, gait abnormalities, neurogenic claudication, bladder or bowel dysfunction. Spinal stenosis is classified as congenital, acquired or combined. There are many causes for this condition; however, the most common cause is degenerative in nature.

For the majority of patients, conservative treatments are tried first. Non-surgical management includes rest, controlled physical activity, back brace, physical therapy, non-steroidal anti-inflammatory medications and epidural injections. Surgical decompression is performed for severe disabling pain not responding to conservative treatment, progressive neurological deficit, bladder or bowel dysfunction due to cauda equina syndrome. Decompressive surgery performed under general anesthesia is not without risks, especially in the degenerative spinal stenosis patients who are usually advanced in age with multiple medical problems.

The intervertebral foramen changes significantly on flexion and extension as well as on lateral bending and axial rotation. Flexion increases central canal and foraminal dimensions, while extension decreases them. Patients seek relief for "neurogenic claudication" or leg pain, which is aggravated by walking and relieved by sitting or flexing the spine forward. Patients with lumbar spinal stenosis assume a more flexed or rounded posture as they walk. They can walk longer periods by leaning forward supported by a cane, walker or shopping cart. Frequently, the stenotic spinal segment is limited to one or two levels and it is not necessary to flex the entire spine forward or round the whole back. If the one or two involved levels of stenosis are flexed forward, the symptoms can be relieved. If only the stenotic spinal segment (or segments) is flexed forward, then an elderly patient who walks with a kyphotic spine or rounded back can stand up straight and walk without difficulty.

The treatment method of the present invention involves placing an implant device as a spacer between the spinous processes. The implant device effectively keeps the stenotic segment in the sitting or flexed position when the patient stands up. Studies of similar approaches have shown that such treatments can be effective for patients with lumbar spinal stenosis who can sit comfortably, but have difficulty standing and walking.

Previous implant devices for interspinous distraction, such as the X-Stop from St. Francis Medical Technologies, Inc., have provided symptomatic relief and improved physical function in a high percentage of patients. (Zucherman et al, Spine. Jun. 15, 2005;30(12):1351-8.) However, the previous implant devices have the potential for causing continued degeneration of the spinous processes, particularly since the interspinous surface of the spinous process is not normally a load-bearing surface. This potential problem is especially a concern in patients with osteoporosis. In addition, the X-Stop has shown an unacceptably high failure rate for treatment of lumbar spinal stenosis caused by degenerative spondylolisthesis. (Verhoof et al, Eur Spine J. February 2008; 17(2): 188-192.)

DESCRIPTION OF THE INVENTION

For the reasons stated above, it would be desirable to provide improved implant devices and methods for interspinous distraction. In particular, it would be desirable to provide an improved implant device that distributes the load of interspinous distraction so that the entire load is not bearing on the interspinous surfaces. To this end, the present invention provides an implant device having a narrow midsection and two wider, flange-shaped outer sections. The wider, flange-shaped outer sections can be tightened to bear against the thicker bony portions of the spinous processes to support some of the load. Optionally, the wider, flange-shaped outer sections can be configured with pins that will penetrate and engage the thicker bony portions of the spinous processes, which will increase the load bearing potential of the wider, flange-shaped outer sections. Additionally, the wider, flange-shaped outer sections and the pins will help to stabilize the joint. The joint stabilization may help to prevent further dislocation of the vertebra that occurs with spondylolisthesis.

BRIEF DESCRIPTION OF THE DRAWINGS

FIGS. 22-26 illustrate an optional feature of the implant device.

DESCRIPTION OF THE INVENTION

Figure 1:
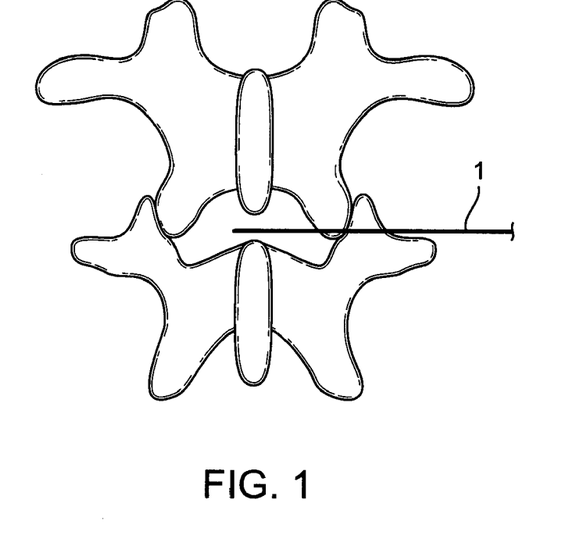
FIG. 1 is a rear or dorsal view of two of a patient's vertebrae showing a wire being inserted between the spinous processes.
Figure 2:
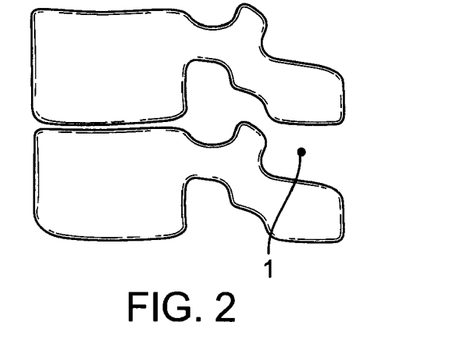
FIG. 2 is a left side lateral view of the patient's vertebrae showing the position of the wire between the spinous processes.

The present invention provides an improved implant device and method of interspinous distraction for treatment of spinal stenosis. The preferred method uses a minimally invasive surgical approach under local anesthesia. The interspinous space is preferably accessed using a percutaneous needle puncture or a small incision from a right lateral approach. Alternatively, the spine can be accessed directly via a midline incision. A wire 1 is placed from the lateral approach as a guide into the space between the spinous processes of the affected vertebrae. FIG. 1 is a rear or dorsal view of two of a patient's vertebrae showing the wire 1 being inserted between the spinous processes. FIG. 2 is a left side lateral view of the patient's vertebrae showing the position of the wire 1 between the spinous processes.

Figures 3, 4:
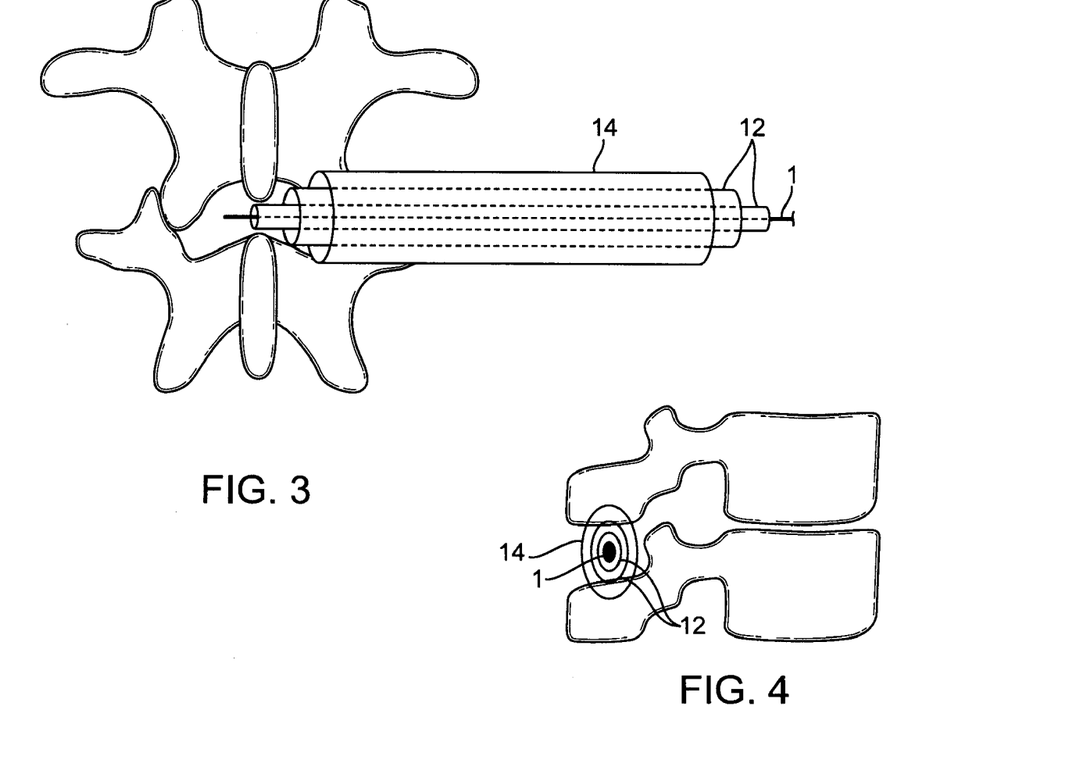
FIG. 3 is a dorsal view showing sequential dilation of a passage through the tissue on the right side of the patient's vertebrae.
FIG. 4 is a right side lateral view showing the position of the passage through the tissue to the patient's vertebrae.

Next, an access passage is formed through the soft tissue from the skin surface or incision on the right lateral side to the spinous processes by sequentially passing a series of tapered dilators 12 coaxially over the wire 1. FIG. 3 is a dorsal view showing sequential dilation of the passage through the tissue on the right side of the patient's vertebrae. FIG. 4 is a right side lateral view showing the position of the passage through the tissue to the patient's vertebrae. The final dilator is configured as a thin-walled access sheath 14 with a large lumen for accessing the interspinous space. Alternatively, the access passage can be dilated with an inflatable cylindrical balloon, then the access sheath 14 can be inserted over the inflated balloon. The tapered dilators 12 and/or the access sheath 14 may have a circular or oval cross section to accommodate the shape of the implant device that will be used.

Figure 5:
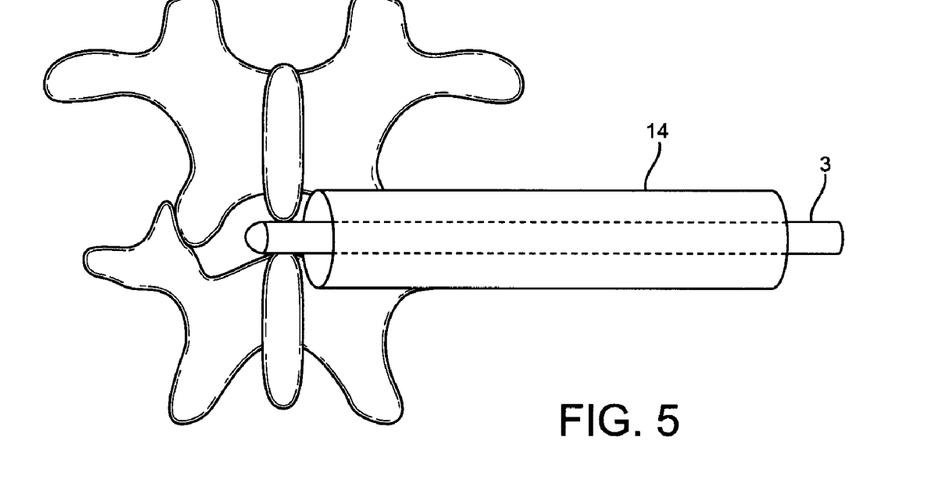
FIG. 5 is a dorsal view of the patient's vertebrae showing the interspinous interval being distracted.

A distractor device 3 is inserted through the lumen of the access sheath 14 to distract or separate the joint between the vertebrae a controlled amount in order to relieve the spinal stenosis. FIG. 5 is a dorsal view of the patient's vertebrae showing the interspinous interval being distracted. This can be done with or without the wire 1 in place. The distractor device 3 may be configured as a tapered pin or as a series of tapered coaxial dilators. Alternatively, the distractor device 3 may be configured as a mechanically-actuated spreader device or as an inflatable cylindrical balloon. During the distraction step, the size of the implant device that will be needed is determined. Optionally, the distractor device 3 may also serve as a gauge for measuring the size of the distracted space.

Figure 6:
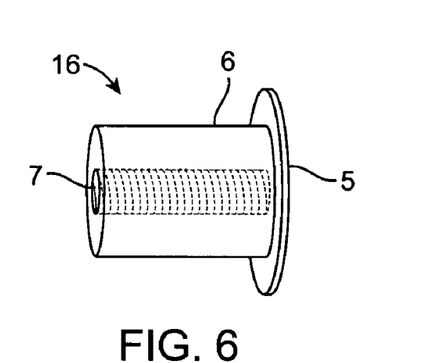
FIG. 6 is a perspective view of a first component of the interspinous distraction implant device, the cage.
Figure 7:
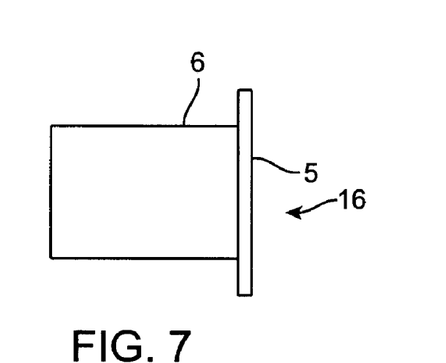
FIG. 7 is a side view of the cage.
Figure 8:
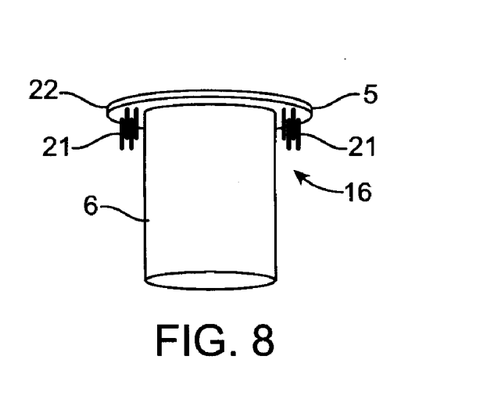
FIG. 8 is a top view of the cage.
Figure 9:
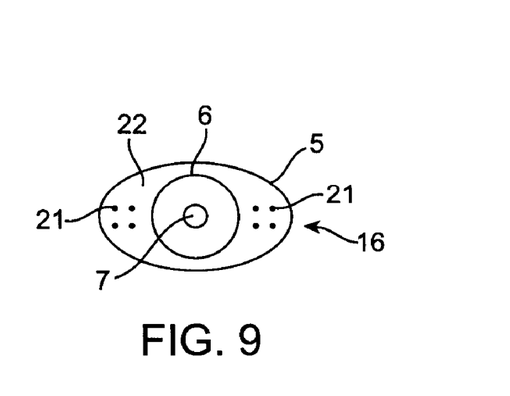
FIG. 9 is an end view of the cage.

Next, the first component of the interspinous distraction implant device, the cage 16, is inserted through the lumen of the access sheath 14 and into the distracted space between the spinous processes. FIG. 6 is a perspective view of a first component of the interspinous distraction implant device, the cage 16. FIG. 7 is a side view of the cage 16. FIG. 8 is a top view of the cage 16. FIG. 9 is a left end view of the cage 16. The cage 16 has a narrow midsection 6 that fits between the spinous processes and a wider, flange-shaped outer section 5. The flange-shaped outer section 5 may be round or oval or another preferred shape. Optionally, as shown in FIGS. 8 and 9, the flange-shaped outer section 5 can be configured with pins or teeth 21 on the medial surface 22 that will penetrate and engage the thicker bony portions of the spinous processes. Alternatively or in addition, the medial surface 22 of the flange-shaped outer section 5 may have a roughened or knurled surface texture to engage the surface of the thicker bony portions of the spinous processes. The narrow midsection 6 may be round or oval in cross section and has a threaded lumen 7 through the interior. Preferably, the cage 16 will also have a feature, such as a slot, cross or hex-shaped recess or the like, aligned with the threaded lumen 7 to allow it to be engaged by a tool during implantation.

Figure 10:
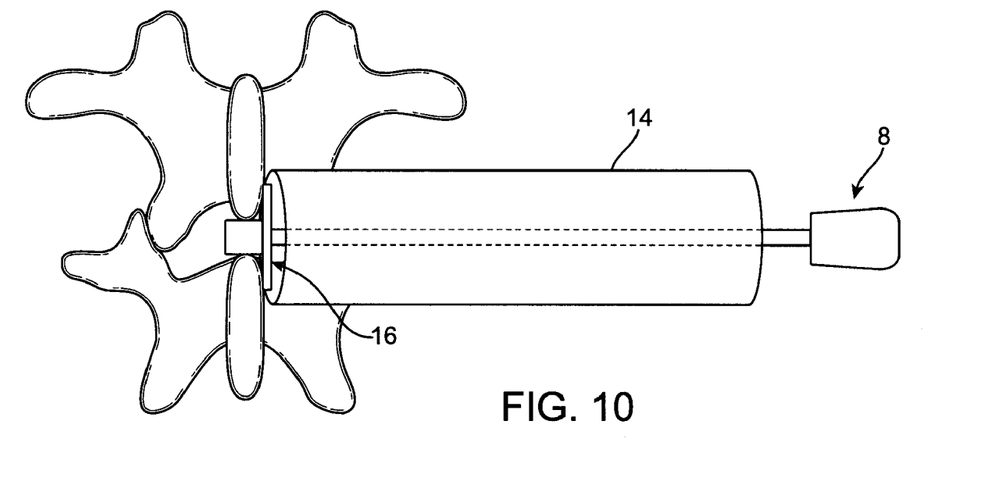
FIG. 10 is a dorsal view showing the cage inserted in the distracted space between the spinous processes with the assistance of a cannulated screwdriver.
Figure 11:
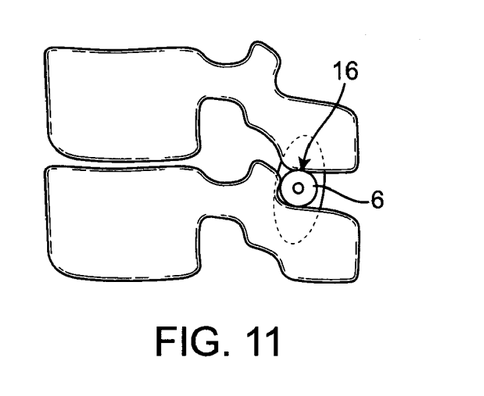
FIG. 11 is a left side lateral view showing the cage inserted between the spinous processes.
Figure 12:
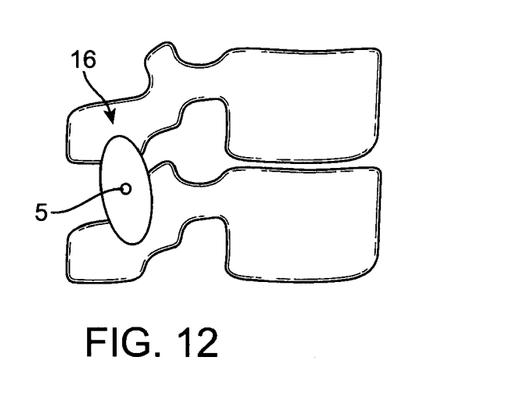
FIG. 12 is a right side lateral view showing the cage inserted between the spinous processes.

FIG. 10 is a dorsal view showing the cage 16 inserted in the distracted space between the spinous processes with the assistance of a cannulated screwdriver 8. The cannulated screwdriver 8 helps to orient the cage 16 as it is being inserted so that it is positioned correctly with respect to the spinous processes. 8 FIG. 11 is a left side lateral view showing the cage 16 inserted between the spinous processes. FIG. 12 is a right side lateral view showing the cage 16 inserted between the spinous processes.

Figure 13:
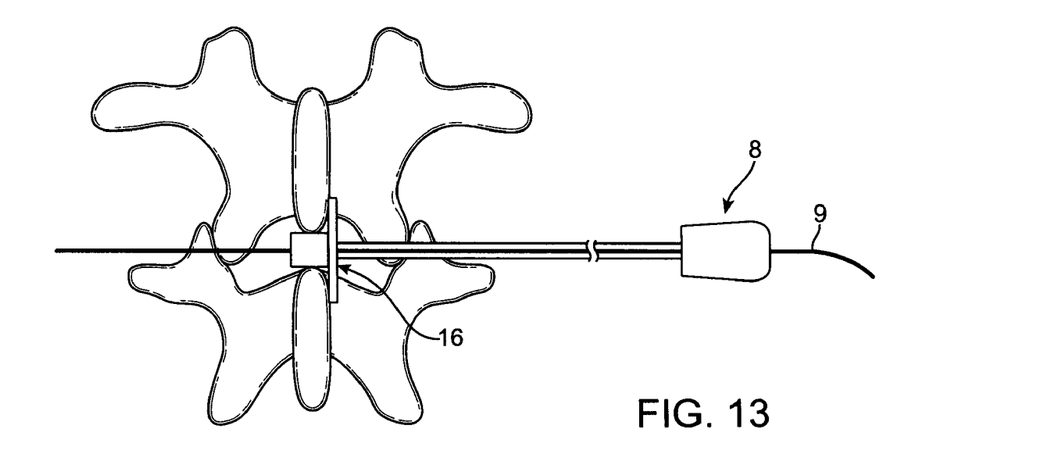
FIG. 13 is a dorsal view showing a wire inserted through the cannulated screwdriver and the cage.
Figure 14:
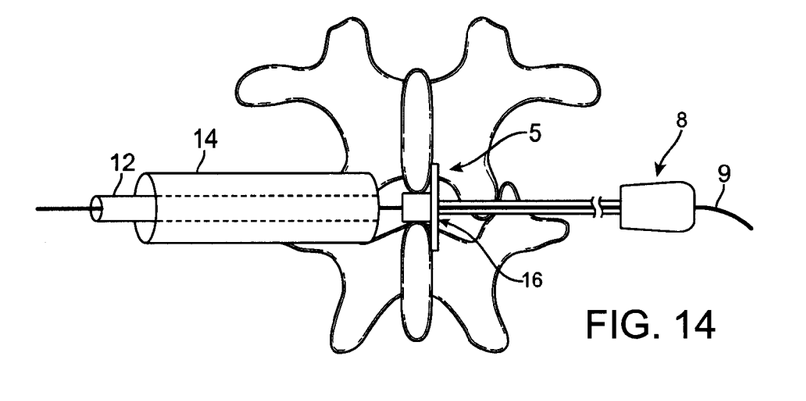
FIG. 14 is a dorsal view showing sequential dilation of a passage through the tissue on the left side of the patient's vertebrae.

As shown in the dorsal view of FIG. 13, a wire 9 is inserted through the cannulated screwdriver 8 and through the threaded lumen 7 of the cage 16 until it comes out through the soft tissue on the left side of the patient's spine. Next, an access passage is formed through the soft tissue from the skin surface on the left lateral side to the spinous processes by sequentially passing a series of tapered dilators 12 coaxially over the wire 1, as previously done on the right side, the final dilator is configured as a thin-walled access sheath 14 with a large lumen for accessing the interspinous space. FIG. 14 is a dorsal view showing sequential dilation of a passage through the tissue on the left side of the patient's vertebrae. Alternatively, the access passage can be dilated with an inflatable cylindrical balloon, then the access sheath 14 can be inserted over the inflated balloon. The step of dilating an access passage through the soft tissue may also be done prior to insertion of the cage 16.

Figure 15:
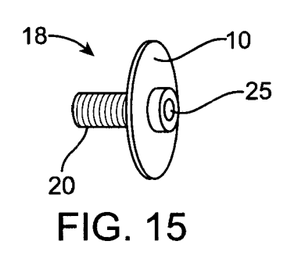
FIG. 15 is a perspective view of a second component of the interspinous distraction implant device, the cap.
Figure 16:
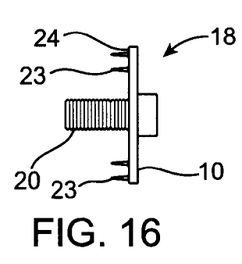
FIG. 16 is a side view of the cap.
Figure 17:
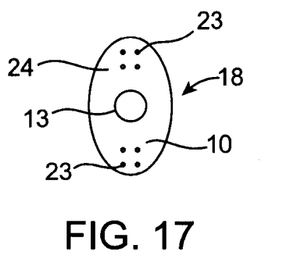
FIG. 17 is an end view of the cap.
Figure 18:
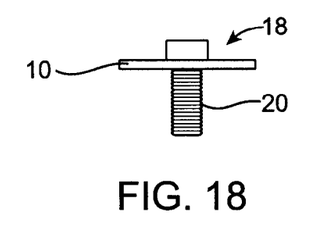
FIG. 18 is a top view of the cap.
Figure 19:
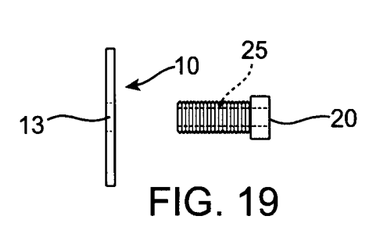
FIG. 19 is an exploded view of the cap.

FIG. 15 is a perspective view of a second component of the interspinous distraction implant device, the cap 18. FIG. 16 is a side view of the cap 18. FIG. 17 is an end view of the cap 18. FIG. 18 is a top view of the cap 18. FIG. 19 is an exploded view of the cap 18. The cap 18 has a flange-shaped outer section 10 with a cannulated screw 20 through a hole 13 in the center. The cannulated screw 20 has a through lumen 25 sized for a sliding fit over the wire 9. The head of the cannulated screw 20 will preferably have a feature, such as a slot, cross or hex-shaped recess or the like, to allow it to be engaged by a tool during implantation. The flange-shaped outer section 5 may be round or oval or another preferred shape, and is preferably the mirror image of the flange-shaped outer section 5 on the cage 16. Optionally, as shown in FIGS. 16 and 17, the flange-shaped outer section 10 of the cap 18 can be configured with pins or teeth 23 on the medial surface 24 that will penetrate and engage the thicker bony portions of the spinous processes. Alternatively or in addition, the medial surface 24 of the flange-shaped outer section 10 may have a roughened or knurled surface texture to engage the surface of the thicker bony portions of the spinous processes.

Figure 20:
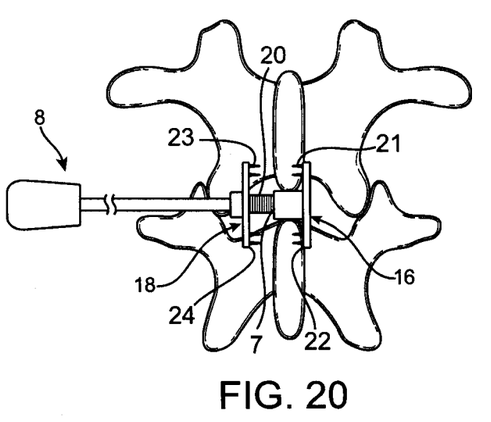
FIG. 20 is a dorsal view showing the cap being fastened to the cage of the implant device.

The cap 18 is inserted through the lumen of the thin-walled access sheath 14 and the fastened to the cage 16 using the cannulated screw 20. Optionally, the wire 9 can be used to align the cannulated screw 20 with the threaded lumen 7 in the cage 16 for ease of assembly. FIG. 20 is a dorsal view showing the cap 18 being fastened to the cage 16 of the implant device. The cannulated screw 20 is tightened into the threaded lumen 7 in the cage 16 using one or two cannulated screwdrivers 8, as needed.

Figure 21:
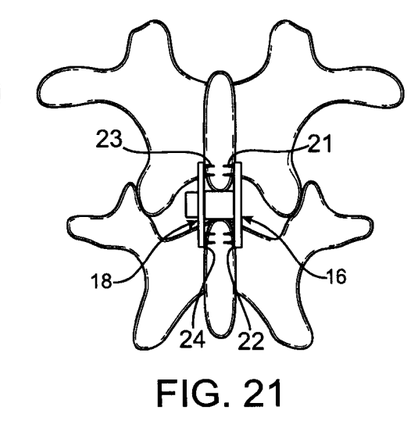
FIG. 21 is a dorsal view showing the implant device implanted between the spinous processes of the patient's vertebrae.
Figure 22:
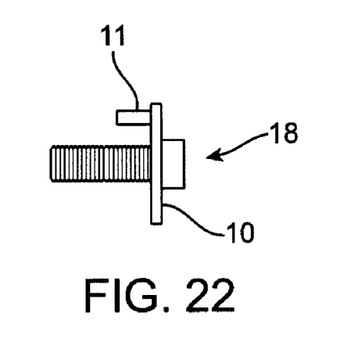
FIG. 22 is a side view of a cap with a key configured to interlock with the cage.
Figure 23:
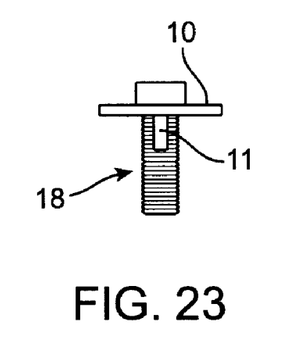
FIG. 23 is a top view of the cap.
Figure 24:
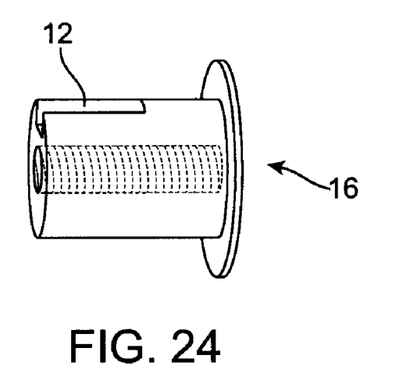
FIG. 24 is a side view of the cage with a slot configured to engage the key on the cap.
Figure 25:
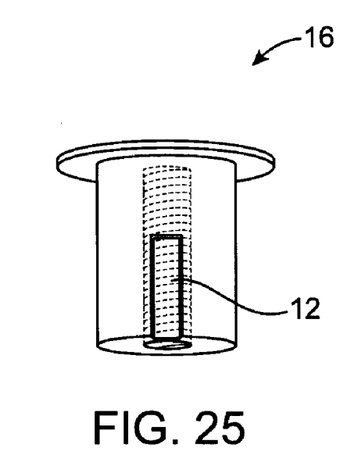
FIG. 25 is a top view of the cage.

FIG. 21 is a dorsal view showing the implant device fully implanted between the spinous processes of the patient's vertebrae. The access sheaths 14 are removed and the tissue openings are closed to complete the procedure.

The length of the midsection 6 of the cage 16 is less than the thickness of the adjacent spinous processes so that the medial surfaces 22, 24 on the flange-shaped outer sections 5, 10 of the cage 16 and cap 18 will contact and engage the surface of the thicker bony portions of the spinous processes to support some of the load when the cannulated screw 20 is tightened into the threaded lumen 7 of the cap 18, as shown in FIGS. 20 and 21. FIGS. 20 and 21 also show how the optional pins or teeth 21, 23 on the cage 16 and cap 18 penetrate and engage the thicker bony portions of the spinous processes increase the load bearing potential of the flange-shaped outer sections 5, 10 when the cannulated screw 20 is tightened into the threaded lumen 7 of the cap 18.

Figure 26:
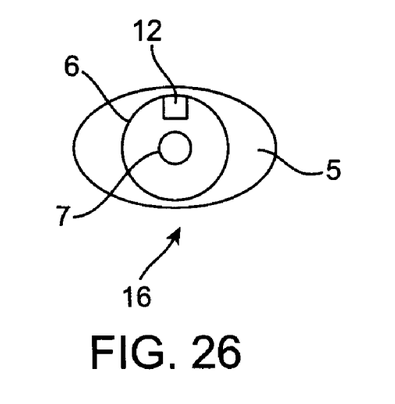
FIG. 26 is a left end view of the cage.

FIGS. 22-26 illustrate an optional feature of the implant device. To prevent rotation, the flange-shaped outer section 10 of the cap 18 over the cage 16, a key 11, or other interlocking feature, is configured to lock into a slot 12 in the cage 16. The key 11 and the slot 12 are preferably located on a lateral side of the implant device away from any load bearing surface of the midsection 6, as shown in FIG. 26. Alternatively or in addition, the slot 12 may be internal to the cage 16 so that it is not exposed on the surface of the midsection 6.

As previously mentioned, the cage 18 can also be placed without dilators and via a midline incision. In this case, only the interspinous distractor and screwdriver need to be placed through a small lateral incision similar to steps described above.

The cage 16, the cap 18 and other components of the implant device can be made of titanium, titanium alloys, stainless steel, cobalt-chromium alloys or other biocompatible metals and/or polymers.

Figure 27:
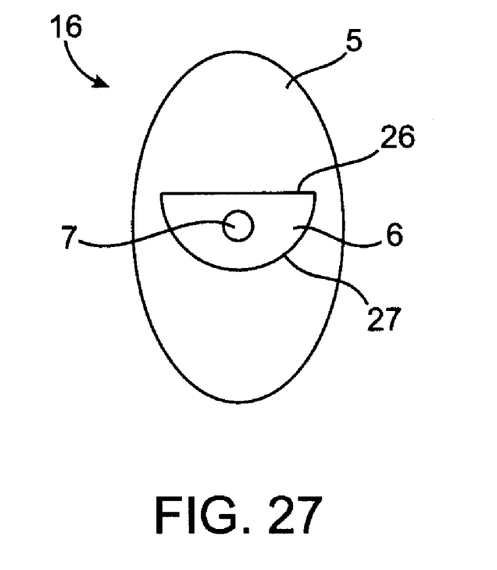
FIG. 27 is a side view of a cage with a midsection having a semicircular or D-shaped cross section.
Figure 28:
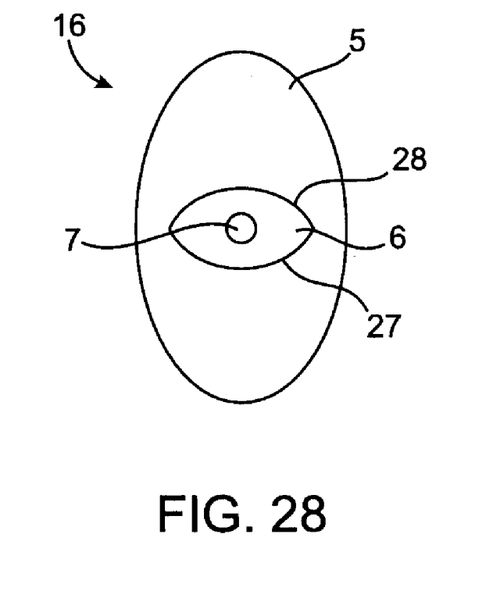
FIG. 28 is a side view of a cage with a midsection having an oval or football shaped cross section.
Figure 29:
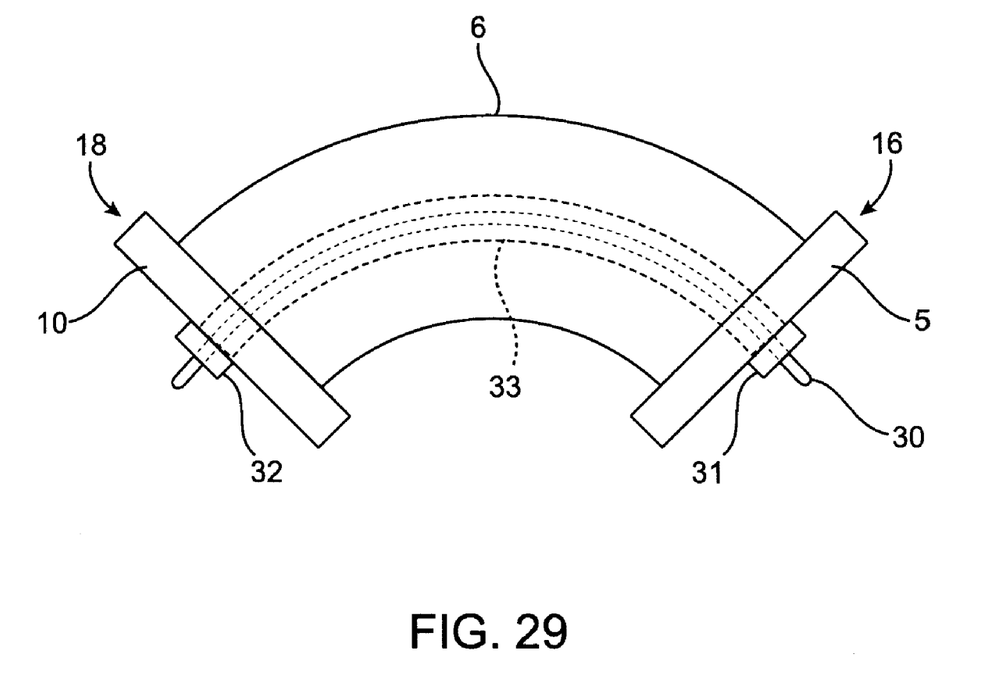
FIG. 29 is a top view of an implant device with a curved midsection.

FIGS. 27-29 show additional optional features of the implant device that can be used separately or combined with other embodiments and features of the invention.

FIG. 27 is a side view of a cage 16 with a midsection 6 having a semicircular or D-shaped cross section. The midsection 6 of the implant device has an approximately flat or gently curved upper surface 26 and an approximately semicircular lower surface 27. The shape of the midsection 6 is intended to distribute the load more effectively on the adjacent spinous processes to reduce further deterioration of the interspinous surfaces. In an alternate embodiment, the midsection 6 of the implant device may be configured with an approximately semicircular upper surface 26 and an approximately flat or gently curved lower surface 27.

FIG. 28 is a side view of a cage 16 with a midsection having an oval or football shaped cross section. The midsection 6 of the implant device has a curved upper surface 28 and a curved lower surface 29 that meet to form a cross section that is an oval or a shape like an American or Rugby football. The upper surface 28 and the lower surface 29 may be configured to have the same curve or they may be configured with different curves. The shape of the midsection 6 is intended to distribute the load more effectively on the adjacent spinous processes to reduce further deterioration of the interspinous surfaces.

FIG. 29 is a top view of an implant device with a curved midsection 6. The features of this embodiment can be used separately or combined with other embodiments and features of the invention described herein. The curved midsection 6 allows the cage 16 and the cap 18 of the implant device to be inserted from incisions closer to the centerline of the patient. In a variation of the procedure described above, an incision or needle puncture is made close to the spine, a wire is inserted and a curving or steeply angled passage is dilated from the insertion point to the interspinous space. After distraction, the curved midsection 6 of the cage 16 is inserted into the passage and the cage 16 is rotated about a cranial-caudal axis to push the curved midsection 6 through the interspinous space. Another passage is dilated from a contralateral point close to the spine where the wire exits to the interspinous space and the cap 18 is inserted through this passage and attached to the cage 16. A cable 30 passes through a curved lumen 33 in the midsection 6 and attaches the cap 18 to the cage 16 with one or more clamps or other cable locking devices 31, 32. Alternatively, the cap 18 may be attached to the cage 16 with a cannulated screw, as described above. Optionally, a key 11 and slot 12 may be used to align the cap 18 with the cage 16, as described in connection with FIGS. 22-26 above. The curvature of the curved midsection 6 and the angle of the first outer section 5 and the second outer section 6 may vary depending on which interspinous space is being treated and the geometry of the adjacent vertebrae.

The improved interspinous distraction implant device and method of treatment for spinal stenosis have numerous advantages. It is a minimally invasive surgical treatment, causing minimum tissue disruption. The implant device can be placed via a midline incision or lateral incision. It is bidirectional, meaning it can be placed from the left or right side of the patient. The cage is very secure due to the larger and stronger outer section and cap. The design allows compression using a screw. Due to the long screw inside the cage, the risk of screw loss is significantly reduced.

The implant device has a low profile and will not interfere with normal spinal function. The implant device sits just at the laminal/spinous process junction where the bone is stronger. The implant device can be placed even if there has been a previous hemilaminectomy.

While the present invention has been described herein with respect to the exemplary embodiments and the best mode for practicing the invention, it will be apparent to one of ordinary skill in the art that many modifications, improvements, combinations and subcombinations of the various embodiments, adaptations and variations can be made to the invention without departing from the spirit and scope thereof.

What is claimed is:

1. Apparatus for interspinous distraction, comprising:
    a wire configured for insertion between two adjacent spinous processes of a patient;
    a dilator component insertable coaxially over the wire and configured for dilating a passage from an insertion point on the patient to a space between the two adjacent spinous processes;
    a first thin-walled access sheath having an internal lumen insertable coaxially over the dilator component;
    a distractor device insertable through the internal lumen of the first access sheath to distract the space between the two adjacent spinous processes;

an implant device, including:
a first implant component having a midsection sized and configured for insertion between the two adjacent spinous processes of a patient, the midsection having a through lumen insertable over the wire, and a flange-shaped first outer section attached at a first end of the midsection, the first outer section having a first medial surface with a first means to contact and engage thick, bony portions of the spinous processes;
a second implant component having a flange-shaped second outer section, the second outer section each having a second medial surface with a second means to contact and engage thick, bony portions of the adjacent spinous processes;
and attachment means for attaching the flange-shaped second outer section to a second end of the midsection of the first implant component.

2. The apparatus for interspinous distraction of claim 1, wherein the first means to contact and engage thick, bony portions of the spinous processes comprises a plurality of pins or teeth extending from the first medial surface of the flange-shaped first outer section that are configured to penetrate and engage the thick, bony portions of the spinous processes, and wherein the second means to contact and engage thick, bony portions of the spinous processes comprises a plurality of pins or teeth extending from the second medial surface of the flange-shaped second outer section that are configured to penetrate and engage the thick, bony portions of the spinous processes.

3. The apparatus for interspinous distraction of claim 1 wherein the first means to contact and engage thick, bony portions of the spinous processes comprises a rough texture on the first medial surface of the flange-shaped first outer section that is configured to contact and engage the thick, bony portions of the spinous processes, and wherein the second means to contact and engage thick, bony portions of the spinous processes comprises a rough texture on the second medial surface of the flange-shaped second outer section that is configured to contact and engage the thick, bony portions of the spinous processes.

4. The apparatus for interspinous distraction of claim 1, wherein the attachment means of the implant device comprises:
a threaded lumen extending through an interior of the midsection of the first implant component;
and a cannulated screw extending through a hole in the flange-shaped second outer section, the cannulated screw being sized and configured for engaging the threaded lumen within the midsection of the first implant component for attaching the flange-shaped second outer section to a second end of the midsection.

5. The apparatus for interspinous distraction of claim 1, wherein the dilator component comprises a series of tapered dilators insertable coaxially over the wire.

6. The apparatus for interspinous distraction of claim 1, further comprising:
a second thin-walled access sheath having a second internal lumen and insertable over the wire from a second insertion point on the patient to a second side of the space between the two adjacent spinous processes.

7. The apparatus for interspinous distraction of claim 6, wherein the first implant component of the implant device is sized and configured for insertion through the internal lumen of the first access sheath, and the second implant component of the implant device is sized and configured for insertion through the internal lumen of the second thin-walled access sheath.

8. The apparatus for interspinous distraction of claim 1, further comprising:
a first cannulated screwdriver insertable through the internal lumen of the first access sheath with a lumen of the first cannulated screwdriver positioned around the wire and having a distal end configured for engaging the first implant component of the implant device;
and a second cannulated screwdriver insertable through the internal lumen of the second access sheath with a lumen of the second cannulated screwdriver positioned around the wire and having a distal end configured for engaging the second implant component of the implant device.

9. An interspinous distraction implant device, comprising:
a first implant component having a midsection sized and configured for insertion between two adjacent spinous processes of a patient and a flange-shaped first outer section attached at a first end of the midsection, the first outer section having a first medial surface with first means to contact and engage thick, bony portions of the spinous processes;
a second implant component having a flange-shaped second outer section, the second outer section each having a second medial surface with second means to contact and engage thick, bony portions of the adjacent spinous processes;
and attachment means for attaching the flange-shaped second outer section to a second end of the midsection of the first implant component;
wherein the midsection of the first implant component is curved such that the flange-shaped first outer section of the first implant component and the flange-shaped second outer section of the second implant component are at an angle with respect to one another;
wherein the attachment means comprises a cable that passes through a lumen in the curved midsection for attaching the flange-shaped second outer section to the second end of the midsection of the first implant component.

10. The interspinous distraction implant device of claim 9, wherein the midsection of the first implant component has a semicircular cross section.

11. The interspinous distraction implant device of claim 9, wherein the midsection of the first implant component has a D-shaped cross section.

12. The interspinous distraction implant device of claim 9, wherein the midsection of the first implant component has a football-shaped cross section with a curved upper surface and a curved lower surface that meet to form a cross section that is a shape like an American football.

13. The interspinous distraction implant device of claim 9, wherein the attachment means further comprises a locking device to lock the cable for attaching the flange-shaped second outer section to the second end of the midsection of the first implant component.

14. The interspinous distraction implant device of claim 9, wherein the attachment means comprises a cannulated screw for attaching the flange-shaped second outer section to a second end of the midsection of the first implant component.

15. The interspinous distraction implant device of claim 9, further comprising:
a key extending from the second implant component and configured to engage a slot in the first implant component to prevent rotation of the second implant component with respect to the first implant component.

* * * * *